US007767787B1

(12) United States Patent
Vollmers et al.

(10) Patent No.: US 7,767,787 B1
(45) Date of Patent: Aug. 3, 2010

(54) SUBSTANCE FOR OBTAINING HIGHLY EFFECTIVE TUMOR MEDICATIONS AS WELL AS A PROCESS

(75) Inventors: Heinz Peter Vollmers, Wuerzburg (DE); Hans Konrad Mueller-Hermelink, Wuerzburg (DE)

(73) Assignee: Debiovision Inc., Montreal, Quebec (CA)

( * ) Notice: Subject to any disclaimer, the term of this patent is extended or adjusted under 35 U.S.C. 154(b) by 0 days.

(21) Appl. No.: 09/469,606

(22) Filed: Dec. 22, 1999

(30) Foreign Application Priority Data

Dec. 22, 1998 (DE) ............................... 198 59 248
Mar. 5, 1999 (DE) ............................... 199 09 771

(51) Int. Cl.
| | |
|---|---|
| C07K 1/00 | (2006.01) |
| C07K 2/00 | (2006.01) |
| C07K 4/00 | (2006.01) |
| C07K 7/00 | (2006.01) |
| C07K 14/00 | (2006.01) |
| C07K 17/00 | (2006.01) |
| A61K 35/14 | (2006.01) |
| A61K 38/00 | (2006.01) |
| A23J 1/00 | (2006.01) |
| C12P 21/08 | (2006.01) |

(52) U.S. Cl. .................... 530/350; 530/300; 530/387.5; 530/387.1; 530/388.2; 530/388.8; 530/395; 530/412

(58) Field of Classification Search ................ 530/300, 530/350, 395, 412, 387.1, 388.2, 388.8, 388.7, 530/385.7
See application file for complete search history.

(56) References Cited

U.S. PATENT DOCUMENTS 5,695,945 A * 12/1997 Tsuji
5,763,224 A   6/1998 Caras et al.

FOREIGN PATENT DOCUMENTS

WO      99 43800      9/1999

OTHER PUBLICATIONS

Medof et al. Inhibition of Complement Activation on the surface of cells after incorporation of decay-accerlerating factor (DAF) into their membranes. J.Exp. Med. 160: 1558-1578, Nov. 1984.*
Karnauchow et al. The HeLa Cell Receptor for Enterovirus 70 is Decay-Accelerating Factor (CD55). Journal of Virology 70(8): 5143-5152, Aug. 1996.*
Knight, Pamela. The Carbohydrate Frontier. BioTechnology 7(1): 36-40, Jan. 1989.*
Bio Abstracts , vol. 1997, abstract No. 68043; L Bjorge et al.: "Compliment-regulatory proteins in ovarian malignancies" & International Journal of Cancer. bd. 70, Nr. 1, 1997, pp. 14-25, new york, NY.

F Hensel et al.: Characterization of glycosylphosatidylinositol-linked molecule CD55/Decay-accelerating factor as the receptor for antibody SC-1 induced apoptosis Cancer Research Bd. 59, Oct. 15, 1999.
Hensel F. et al. *Lab. Invest.*, vol. 81, No. 11, pp. 1553-1563 (2001): "Regulation of the new coexpressed CD55(decay-accelerating factor, DAF) receptor on stomach carcinoma cells involved in antibody SC-1-induced apoptosis".
Caras IW. et al., *Nature.*, vol. 325, pp. 545-549 (Feb. 5, 1987): "Cloning of decay-accelerating factor suggests novel use of splicing to generate two proteins".
Hensel F. et al., *Cancer Research.*, vol. 59, pp. 5299-5306 (Oct. 15, 1999): "Characterization of Glycosylphosphatidylinositol-linked Molecule CD55/Decay-accelerating Factor as the Receptor for Antibody SC-1-induced Apoptosis".
Lass JH. et al., *Invest. Ophthalmol. Vis. Sci.*, vol. 31, No. 6, pp. 1136-1148 (1990): "Expression of two molecular forms of the complement decay-accelerating factor in the eye and lacrimal gland" Abstract Only.
Lublin DM. et al., *J. Immunol.*, vol. 137, No. 5, pp. 1629-1635 (1986): "Biosynthesis and glycosylation of the human complement . . . " Abstract Only.
Sugita Y. et al., *J. Immunol. Methods.*, vol. 104 No. 1-2, pp. 123-130 (1987): "Isolation of decay-accelerating factor . . . " Abstract Only.
Kinoshita T et al., *J. Immunol.*, vol. 138, No. 9., pp. 2994-2998 (1987): "A high m.w. form of decay-accerating factor . . . " Abstract Only.
Nicholson-Weller A et al., *J. Immunol.*, vol. 127, No. 5., pp. 2035-2039(1981): "Purification from guinea pig erythrocyte stroma . . . " Abstract Only.
Coyne et al., "Mapping of Epitopes, Glycosylation Sites, and Complement Regulatory Domains in Human Decay Accelerating Factor," *J. Immun.*, 149(9):2906-2913 (1992).
Hara et al., "A Monoclonal Antibody Against Human Decay-Accelerating Factor (DAF, CD55), D17, which Lacks Reactivity with Semen-DAF," *Immun. Letters*, 37:145-152 (1993).
Spendlove et al., "Decay Accelerating Factor (CD55): A Target for Cancer Vaccines?," *Cancer Res.*, 59:2282-2286 (1999).
Hensel et al., "Mitogenic Autoantibodies in *Helicobacter pylori*-Associated Stomach Cancerogenesis," *Int. J. Cancer* 81(11):229-235 (1999).
Hermann et al., "Deactivation of Regulatory Proteins hnRNP A1 and A2 During SC-1 Induced Apoptosis," *Human Antibodies* 10:83-90 (2001).
Medof et. al., "Identification of the Complement Decay-Accelerating Factor (DAF) on Epithelium and Glandular Cells and in Body Fluids," *J. Exp. Med* 165:848-864 (1987).
Pfaff et al., "Human Monoclonal Antibody against a Tissue Polypeptide Antigen-Related Protein from a Patient with a Signet-Ring Cell Carcinoma of the Stomach," *Cancer Research* 50:5192-5198 (1990).
Vollmers and Birchmeier, "Monoclonal Antibodies Inhibit the Adhesion of Mouse B 16 Melanoma Cells in vitro and Block Lung Metastasis in vivo," *Proc. Natl. Acad. Sci. USA* 80:3729-3733 (1983).

(Continued)

*Primary Examiner*—Alana M Harris
(74) *Attorney, Agent, or Firm*—Clark & Elbing LLP; Kristina Bieker-Brady; Jan N. Tittel

(57) ABSTRACT

The invention relates to a substance and a process for obtaining anti-tumor agents.

18 Claims, 17 Drawing Sheets

OTHER PUBLICATIONS

Vollmers et al., "Adjuvant Therapy for Gastric Adenocarcinoma with the Apoptosis-Inducing Human Monoclonal Antibody SC-1: First Clinical and Histopathological Results," *Oncology Reports* 5:549-552 (1998).

Vollmers et al., "Apoptosis of Stomach Carcinoma Cells Induced by a Human Monoclonal Antibody." *Cancer* 76(7):550-558 (1995).

Vollmers et al., "SC-1, a Functional Human Monoclonal Antibody against Autologous Stomach Carcinoma Cells," *Cancer Research* 49:2471-2476 (1989).

Vollmers et al., "Tumor-Specific Apoptosis Induced by the Human Monoclonal Antibody SC-1: A New Therapeutical Approach for Stomach Cancer," *Oncology Reports* 5:35-40 (1998).

* cited by examiner

[Key:]

Verdünnungsreihe = dilution series

[Key:]

Ca$^{2+}$ konzentration [nM] = Ca$^{2+}$ concentration [nM]

Zeit [sec] = Time [sec]

[Key:]

Relative Aktivität [%] = relative activity [%]

Zeit [h] = Time [h]

Figur 13

SUBSTANCE FOR OBTAINING HIGHLY EFFECTIVE TUMOR MEDICATIONS AS WELL AS A PROCESS

The invention relates to a substance as well as a process for obtaining anti-tumor agents.

Gastric carcinoma is one of the most common types of cancer worldwide. According to Lauren in "The Two Histological Main Types of Gastric Carcinoma," Acta Path Microbiol Scand; 64: 331-49, they are histologically divided into diffuse adenocarcinomas and intestinal adenocarcinomas. Intestinal gastric carcinomas are often accompanied by chronic gastritis B and especially by intestinal metaplasias, which are considered to be precursors of dysplastic alterations and of gastric carcinomas. Differences between these two types are also indicated in that patients with carcinomas of the diffuse type often belong to blood group A, from which it can be deduced that genetic factors influence the risk of cancer, while environmental factors, e.g., a *Helicobacter pylori* infection, are possibly of importance for the development of carcinomas of the intestinal type. It is noted that gastric-adenocarcinomas are becoming less common in the West but are now on the rise in the East.

Up until now, therapy has been limited to gastrectomy and lymphadenectomy, but because of the still poor prognosis, there is a need for a new accompanying therapy. Immunological studies have shown that even in cases in which the immune system cannot effectively control malignant cells, a cellular and humoral activity can be measured, which is not sufficient, however, to destroy the tumor cells. A more effective effort is now to isolate the antibodies that originate from the immune response of the patient, to reproduce them in a suitable manner and to use them therapeutically. Thus, for example, antibodies that originate from patients with lung, esophageal and colon cancer were isolated, and human monoclonal antibodies that influence, e.g., direct differentiation and the growth of the tumor cells, but which in most cases have the problem of interaction with other tumors or healthy cells, were derived from them.

It is known that human monoclonal SC-1 antibodies can trigger apoptosis in gastric carcinoma cells (Vollmers et al., Cancer 49 (1989), 2471-2476). The antibody reacts with almost all adenocarcinomas of diffuse type and about 20% of the adenocarcinomas of intestinal type (Vollmers et al., Cancer 76 (1995), 550-558; Vollmers et al., Cancer 79 (1997), 433-440). In clinical studies, it was found that antibody SC-1 is able to induce a tumor-specific regression and apoptosis in primary stomach cancer without toxic cross-reactivity relative to normal tissue (Vollmers et al., Oncol. Rep. 5 (1998), 549-552).

Apoptosis is the programmed cell death, suicide of cells, by fragmentation of the DNA, plasmolysis and dilatation of the endoplasmatic reticulum, followed by cell fragmentation and the formation of membrane vesicles, the so-called apoptotic elements. Apoptosis, the physiological form of cell death, ensures a quick and smooth removal of unnecessary cells without triggering inflammatory processes or tissue damages as in the case of necrosis. Under pathological conditions, it is also used to remove malignant cells, such as, for example, cancer precursor cells. It can be triggered by the most varied stimuli, such as, for example, by cytotoxic T-lymphocytes or cytokines, such as tumor necrosis factors, glucocorticoids and antibodies. It is the most common cause of death of eucaryotic cells and occurs in embryogeneses, metamorphoses and tissue atrophy. Apoptotic receptors on the cell surface, such as that of the NGF/TNF family, are predominantly expressed in lymphocytes, but are also found in various other cell types, and thus they are not suitable for cancer treatment. In in-vivo tests, ligands and antibodies for these receptors have led in particular to liver damage. Tumor-specific receptors with an apoptotic function are therefore especially important.

The cellular receptor of monoclonal antibody SC-1 was previously not known. Within the scope of the studies that resulted in this invention, it was possible to identify this cellular receptor. This identification turned out to be difficult, however. On the one hand, monoclonal antibody SC-1 reacts with its receptor only under quite specific stringency conditions in the Western-blot analysis. On the other hand, unspecific reactions that are caused by denaturation artifacts are found with a number of other proteins.

The cellular receptor of antibody SC-1 is an isoform of the protein CD55/DAF that is specific for tumor cells, especially for gastric carcinoma cells (Medof et al., J. Exp. Med. 160 (1984), 1558-1578; Caras et al., Nature 325 (1987), 545-549; Bjorge et al., Int. J. Cancer 70 (1997), 14-25), which does not occur in normal tissue. The specific receptor properties of this isoform are based on a special glycostructure that is connected with the protein backbone via an N-linkage. The tumor-specific receptor can be used in a screening process for identifying specific binding partners. Specific partners for binding to the receptor are those substances within the meaning of this invention that bind selectively to a tumor-specific glycostructure but not significantly to a glycostructure of CD55/DAF that occurs in normal cells and preferably have the ability to induce apoptosis. These specific binding partners can be used for the production of therapeutic agents for inducing apoptosis and/or for combatting tumors as well as for the production of diagnostic agents.

The binding of antibody SC-1 to the tumor-specific N-linked glycostructure of the CD55/DAF protein induces a tyrosine phosphorylation of three proteins and the activation of caspase-3 and caspase-8. In addition, it was found that the apoptosis induced by antibody SC-1 leads to a transient increase of the presentation of tumor-specific N-glycosylated CD55/DAF on the surface of tumor cells. This increased presentation can be caused by an increased expression and/or by an increased glycosylation. The tumor-specific N-glycosylated CD55/DAF protein then disappears from the cell membrane by endocytosis. In addition, a cleavage of cytokeratin 18, an increased expression of c-myc and a reduction of the expression of topoisomerase II$\alpha$ and thus an at least partial cell cycle arrest are observed. The apoptotic processes that are induced by SC-1 do not result in an increased cleavage of poly (ADP-ribose)-polymerase (PARP). In addition, an increase of the intracellular $Ca^{2+}$ concentration, which is released from an intracellular $Ca^{2+}$ pool, is found. An inhibition of the $Ca^{2+}$ release inhibits the apoptosis that is induced by SC-1.

A first aspect of the invention relates to a glycoprotein that comprises at least one section of the amino acid primary structure of CD55/DAF, especially the membrane-bonded isoform DAF-B and a glycostructure that is specific for tumor cells, especially such a glycostructure that reacts with monoclonal Oh antibody SC-1. In SDS-polyacrylamide-gel electrophoresis (under reducing conditions), such a glycoprotein that can be obtained from, for example, human adenocarcinoma cell line 23132 (DSM ACC 201) or from other human adenocarcinoma cell lines, such as 3051 (DSM ACC 270) or 2957 (DSM ACC 240) or from primary tumor cells of gastric adenocarcinoma patients has an apparent molecular weight of about 82 kD. In addition to this 82 kD f protein, the invention also relates to variants with deletions, insertions and/or substitutions in the amino acid primary structure, which, however, have a glycostructure that is analogous to the natural protein, i.e. tumor-specific and preferably reactive with antibody SC-1.

The glycoprotein according to the invention can be obtained by membrane preparations being produced from cells that express a protein with the desired glycostructure, e.g., from cells of human adenocarcinoma cell line 23132 or from other human adenocarcinoma cell lines, and the glycoprotein is obtained from this by chromatographic processes, e.g., by size-exclusion and/or anion-exchange chromatography. The production of the membrane preparations is carried out preferably by lysis of cells in hypotonic buffer, ultrasound treatment and subsequent separation of the nuclei. The membrane preparations can be isolated from the remaining extract by centrifuging and further purified by chromatographic methods.

The tumor-specific CD55/DAF-glycoprotein can be used in a test process, in which the ability of a substance to bind to the tumor-specific glycoprotein, especially to its glycostructure, is determined. The test process can be automated as a high-throughput-screening process. In this respect, the glycoprotein can be used in isolated form, as a cell extract, in particular as a membrane preparation or in the form of complete cells, in particular of human adenocarcinoma cell line 23132 or another human adenocarcinoma cell line, or a heterologous eucaryotic cell that is transformed with the CD55 gene, e.g., a mammal cell, which is able to produce a protein with the correct glycostructure. As a control, the binding of the tested substance to a non-tumor CD55/DAF-glycoprotein can be examined, which can be obtained from normal human cells or cell lines. Substances that bind selectively to the tumor-specific glycoprotein are suitable for the production of therapeutic and/or diagnostic agents.

In addition, the ability of the tested substance to induce apoptosis, especially in tumor cells, and/or the ability to induce a phosphorylation cascade that is mediated by CD55/DAF is q, preferably determined. The induction of the apoptosis can be performed by morphological cell studies, by apoptosis test processes, e.g., by an adhesion test (Vollmers et al., Cell 40 (1985), 547-557) determining the keratin-1 and DNA-fragmentation, or by proliferation tests such as the MTT-proliferation test. As an alternative, a determination of caspase activities, for example activities of caspase-3 and/or caspase-8 or a determination of the intracellular free calcium concentration can also be carried out. Substances that selectively induce an apoptosis of tumor cells can be used as anti-tumor-action substances. The induction of the phosphorylation cascade can be monitored by use of antibodies that are specific for phosphorus groups, e.g., phosphotyrosine and/or phosphoserine groups.

Pharmacologically compatible substances are suitably tested. These include low-molecular pharmacological active ingredients, but especially peptides, peptide mimetic agents, antibodies, e.g., polyclonal, monoclonal or recombinant antibodies, antibody fragments or antibody derivatives. Other examples of ligands of the CD55/DAF receptor are aptamers (NexStar Pharmaceuticals, 2860 Wilderness Place, Boulder, Colo. 80301, USA) and spiegelmers (Noxxon Pharma, Gustav-Meyer-Allee 25, 13355 Berlin). Especially preferred, for example, are recombinant antibodies, such as, for example, single-chain scFv-antibodies, as they can be produced in, for example, bacteria cells such as, for example, *E. coli* (Plückthun, Bio/Technology 9 (1991), 545-551 and bibliographic references that are cited therein) or else in eucaryotic host cells (Reff, Curr. Opinion Biotech. 4 (1993), 573-576 and Trill et al., Curr. Opinion Biotech 6 (1995), 553-560 or bibliographic references that are cited therein). In addition, human antibodies, i.e., antibodies with human constant domains, are preferred, as they are produced in the human body, e.g., of carcinoma patients, or chimera and humanized antibodies, in which originally present non-human constant domains and/or framework regions were exchanged by corresponding human areas. Examples of antibody fragments are Fab-, F(ab)$_2$- or Fab'-fragments, as they can be obtained by proteolytic cleavage of antibodies. The antibody derivatives include, for example, conjugates of antibodies with labeling groups and/or effector groups; for example toxic substances such as, for example, choleratoxin or pseudomonas Exotoxin A or radioactive substances.

Another aspect of the invention is the use of substances that bind specifically to tumor glycoprotein CD55/DAF according to the invention (with the exception of already known monoclonal antibody SC-1) for the production of the apoptosis-inducing agents and/or for the production of anti-tumor agents and/or for the production of agents for tumor diagnosis. A tumor-specific or tumor-selective binding within the context of this application preferably means that in immunohistochemical detection, a substance reacts with tumor cells but not significantly with other cells. An induction of the apoptosis within the context of this application means an increase of the apoptosis index, i.e., the proportion of apoptotic cells after treatment with the substance compared to the proliferating cells is higher than without treatment, preferably higher than 50%. The spontaneous apoptosis index without treatment is significantly below 10%, whereby the detection of proliferating cells can be done with antigen Ki67.

Still another aspect of the invention is a process for the preparation of agents that induce apoptosis and/or anti-tumor agents and/or for the production of agents for tumor diagnosis, whereby a potentially active substance is tested on its ability for specific binding to a glycoprotein according to the invention, and in the case of a positive test result, the substance is converted into a form for dispensing that is suitable for pharmaceutical applications optionally together with commonly used adjuvants, additives and vehicles.

Suitable pharmaceutical forms for dispensing contain the active ingredient in a therapeutically effective quantity, especially in an anti-tumor-action quantity. The dose that is administered to a patient and the treatment time depend on the type and severity of the disease. Suitable dosages for the administration of antibodies are described in, for example, Ledermann et al. (Int. J. Cancer 47 (1991), 659-664) and Bagshawa et al. (Antibody, Immunoconjugates and Radiopharmaceuticals 4 (1991), 915-922).

The active ingredient can be administered alone or in combination with other active ingredients either simultaneously or sequentially. In addition to the active ingredient, the pharmaceutical composition can contain other pharmaceutically common substances. The composition can be administered, for example, orally, nasally, via a pulmonary pathway or by injection. Compositions that can be administered orally can be present in the form of tablets, capsules, powders or liquids. Compositions that can be administered by injection are usually in the form of a parenterally compatible aqueous solution or suspension.

In addition, the invention relates to a process for combatting tumors, whereby an anti-tumor-action quantity of a substance that can bind specifically to a glycoprotein according to the invention with the exception of monoclonal antibody SC-1 is administered to a patient, especially a human patient.

Binding partners for tumor-specific CD55/DAF proteins can also be used for diagnostic purposes, e.g., for tumor imaging. Suitable methods for tumor imaging are described in, e.g., Steinstraesser et al. (Clinical Diagnosis and Laboratory Medicine 2 ((1989), 1-11). In this respect, the binding partners are preferably used in the form of conjugates with labeling groups, e.g., radioactive or fluorescent labeling groups. As an alternative, the binding partners can also be incubated in unconjugated form with the sample that is to be tested, and then stained with a secondary binding reagent.

A subject of the invention is thus a process for the diagnosis of tumors, whereby a sample that is to be tested, e.g., a bodily fluid or a tissue sample, or a patient can be brought into contact with a substance that can be bonded to a tumor-specific CD55/DAF glycoprotein, and the presence, the localization and/or the quantity of the glycoprotein in the sample or in the patient can be detected.

The use of substances that specifically bind tumor glycoprotein CD55/DAF to trigger a phosphorylation cascade is also a subject of the invention. Still another subject of the invention is the use of substances that bind specifically to tumor glycoprotein CD55/DAF for transient increase of the presentation of tumor glycoprotein CD55/DAF to the cell surface, which can be caused by an increased glycosylation and/or expression. The tumor-specific glycoprotein then disappears from the cell surface. Still another subject of the invention is the use of substances that bind selectively to tumor glycoprotein CD55/DAF to increase the intracellular calcium level. Substances that bind specifically to tumor glycoprotein CD55/DAF can also be used as agents for cell cycle arrest. Finally, the invention also relates to the use of substances that bind specifically to tumor glycoprotein CD55/DAF to induce apoptotic processes that do not include any cleavage of PARP. The substance can optionally be used as conjugates with labeling groups and/or effector groups.

Still another subject of the invention is the use of substances that bind specifically to tumor glycoprotein CD55/DAF, especially antibody SC-1 for inducing apoptosis in dormant tumor cells. As far as the inventor knows, this finding is not known to date for any tumor-selective substance.

The substances that bind tumor-specific glycoprotein CD55/DAF preferably contain multiple, i.e. at least two, binding sites for CD55/DAF. For example, the substances can contain three, four, five, six, seven, eight, nine, ten or more binding sites, so that a cross-linking is produced in binding to intracellular tumor-specific CD55/DAF. To obtain substances with multiple binding sites, binding molecules can optionally be cross-linked. The cross-linking can be carried out by, for example, chemical coupling with, e.g., bifunctional linker molecules or with highly affine interactions, e.g., streptavidin/biotin. Even if the CD55/DAF binding molecules are, for example, antibodies, e.g., IgG or IgM, that already contain several binding sites, an improvement of the apoptosis induction can be achieved by cross-linking with, e.g., anti-IgG or anti-IgM antibodies. The use of cross-linked antibodies is therefore preferred.

Cell line 23132 can be obtained from the Deutschen Sammlung für Mikroorganismen und Zellkulturen GmbH [German Collection of Microorganisms and Cell Cultures Gmbh], Braunschweig [Brunswick], under file number DSM ACC 201.

In addition, the invention is explained by the examples and figures below. Here:

FIG. 1 shows: the identification of antigens that are reactive with antibody SC-1.

a. Purification of SC-1 antigens from membrane extracts of gastric carcinoma cell line 23132.

b. Sequencing of an 82 kD protein that is identified as an SC-1 antigen by nanoelectrospray-tandem-mass spectroscopy.

FIG. 2 shows: the influence of a cleavage of GPI anchors by phosphatidylinositol-specific phospholipase C (PI-PLC) on a staining with SC-1. Untreated gastric carcinoma cells of cell line 23132 stained with SC-1 (a) and anti-EMA (c); cells that are treated with PI-PLC and stained with SC-1 (b) and anti-EMA (d) (400× magnification).

FIG. 3 shows: the result of an MTT test with antibody SC-1 in gastric carcinoma cells. Control: untreated cells; SC-1: cells treated with SC-1; SC-1, PIPLC: cells treated with phospholipase and then with SC-1.

FIG. 4 shows: the result of an analysis of transient transfixed cells with a CD55-antisense vector. Cells that were transfixed with a control vector show a normal staining pattern with SC-1 (a) and anti-CEA (c). In cells that are transfixed with the antisense vector, the staining with SC-1 is reduced (b), while no change in the staining with anti-CEA (d) can be detected.

FIG. 5 shows: the result of a Klenow fragmentation test. Transfixed cells show no apoptosis without induction with SC-1 (e) in comparison to a positive control (f). After incubation with SC-1, the cells that are transfixed with the control vector indicate apoptosis (g), while the majority of the cells that are transfixed with the CD55 antisense vector are resistant to apoptosis (h).

FIG. 6 shows: a quantitative determination of the apoptosis that is induced by SC-1. Cells that were transfixed with the control and the CD-55 antisense vector were incubated with SC-1, and cytospins of these cells were stained with the Klenow DNA fragmentation kit. The percentages of apoptotic cells were determined by two different individuals by counting apoptosis-positive and negative cells in three different fields with about 500 cells in each case.

FIG. 7 shows: the action of a deglycosylation on the binding of antibody SC-1.

a: Tumor cells incubated with buffer and stained with SC-1;

b: cells incubated with N-glycosidase and with SC-1;

c: cells incubated with buffer and anti-CD55 and d: tumor cells incubated with N-glycosidase and anti-CD55.

FIG. 8 shows: the result of an MTT test with SC-1 in gastric carcinoma cell line 23132.

a: Titration of SC-1;

b: Cross-linking of SC-1 with rabbit-anti-human-IgM-antibodies;

FIG. 9 shows: the change in intracellular calcium concentration after induction of cell line 23132 with SC-1. At point 1, the addition of SC-1 or control antibodies is carried out. At point 2, the cells were washed with Ringer's solution.

FIG. 10 shows: the expression and activity patterns of caspase-3 and caspase-8 after induction with SC-1.

a. Western-blot analysis of caspase-3 and caspase-8. The activation of caspase-3 based on proteolytic cleavage can be detected by the production of the p20 cleavage product.

b. The result of an activity determination of caspase-8. A four-fold increase of caspase-8 activity was found 20 hours after apoptosis was induced.

FIG. 11 shows: the phosphorylation pattern of cell line 23132 after apoptosis is induced.

a: A quick phosphorylation of tyrosine radicals in proteins with molecular weights of about 110 kD and 60 kD as well as the dephosphorylation of a serine radical in a protein with about 35 kD was found after apoptosis was induced with SC-1.

b: An increase of phosphorylation of a tyrosine radical in a 75 kD protein with a maximum after 10 minutes was found after apoptosis was induced.

FIG. 12 shows: an expression and mutation analysis of p53.

a: 5 minutes after apoptosis was induced by SC-1, a significant increase of the mRNA concentration was found, while the high p53 protein concentrations remain unchanged.

b: A sequential analysis of p53 showed a mutation in codon 273, which results in an amino acid exchange from Arg to His.

a: CD55/DAF expression (staining with SC-1)

b: cleavage of PARP (staining with anti-PARP-antibodies)

c: staining with anti-topoisomerase IIα-antibody as a marker for cellular proliferation d: c-myc expression (staining with anti-c-myc-antibody)

Figure 15:

FIG. 15: the action of the caspase-3 inhibitor Ac-DEVD-CHO on the SC-1-induced apoptosis.

Figure 16:
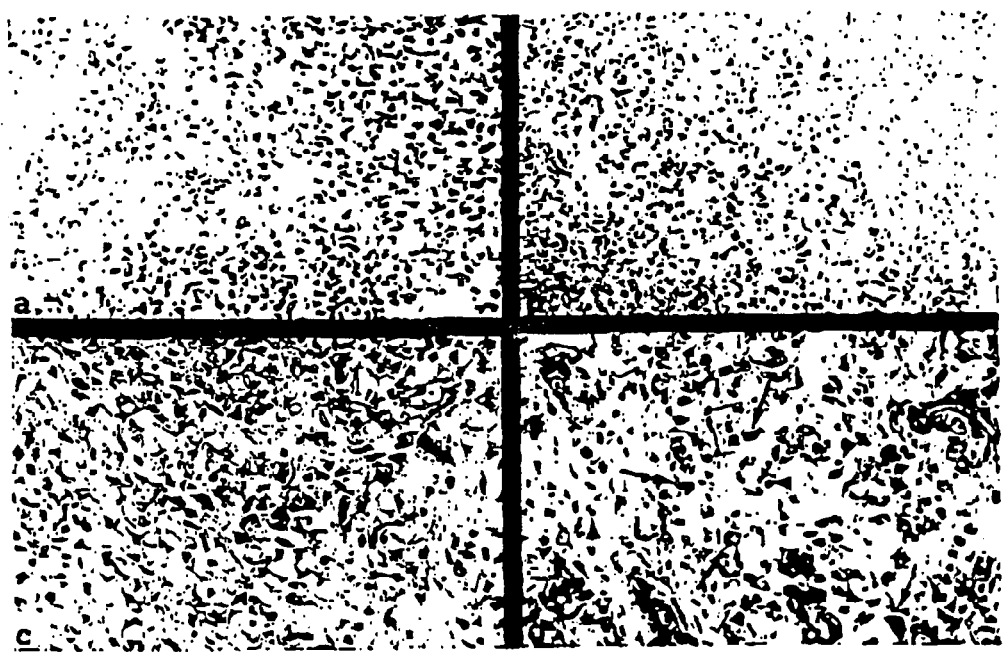

FIG. 16: the detection of a tumor cell-specific apoptosis by in-situ nucleus staining produced by administration of antibody SC-1 on a primary tumor.

Figure 17:
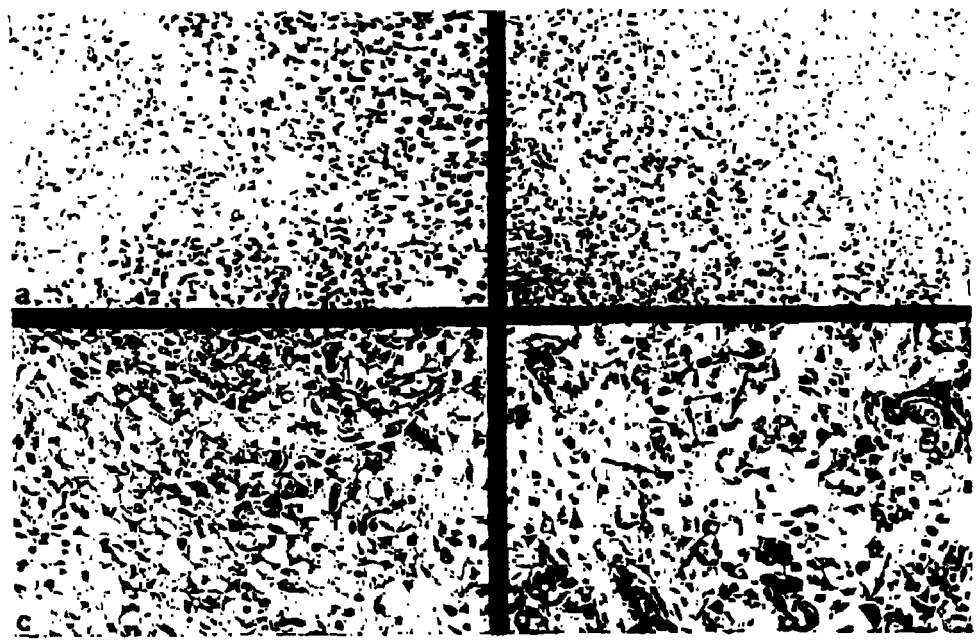

FIG. 17: the action of the administration of antibody SC-1 on a primary tumor.

a: Biopsy sample before administration of SC-1 (in situ staining for apoptosis)

b: primary tumor after administration of SC-1 (in situ staining for apoptosis)

c: biopsy before administration of SC-1 (histological regression analysis)

d: primary tumor after administration of SC-1 (histological regression analysis).

EXAMPLES

1. Material and Methods

1.1 Cell Culture

For all tests, the established gastric-adenocarcinoma cell line 23132 was used (Vollmers et al., Virchows Arch. B. Zell. Pathol. Incl. Mol. Pathol. 63 (1993), 335-343). The cells were cultivated in RPMI-1640 with 10% fetal calf serum and penicillin/streptomycin (both 1%) until a subconfluence occurred. For the described test process, cells were dissolved with trypsin/EDTA and washed twice with phosphate-buffered salt solution (PBS) before use. Human hybridoma cell line SC-1 was produced and cultivated as described in Vollmers et al. (Cancer Res. 49 (1989), 2471-2476).

1.2 Purification of Antibody SC-1

Human monoclonal antibody SC-1 was purified from mass cultures with use of cation-exchange chromatography followed by gel filtration, as described in Vollmers et al. (Oncology Reports 5 (1998), 35-40).

1.3 Purification of the SC-1 Receptor

For preparation of membrane proteins, harvested cells in hypotonic buffer (20 mmol of HEPES, 3 mmol of KCl, 3 mmol of $MgCl_2$) were resuspended, incubated for 15 minutes on ice and ensonified for 5 minutes. The nuclei were pelletized by centrifuging (10,000 g, 10 minutes). The membranes were pelletized by centrifuging (30 minutes, 100,000 g) and resuspended in membrane lysis buffer (50 mmol of HEPES, pH 7.4, 0.1 mmol of EDTA, 1 M of NaCl, 10% glycerol and 1% Triton X-100). Complete® protease inhibitor (Boehringer Mannheim, Germany) was added to all solutions.

The purification of the antigens was carried out by column chromatography with use of an FPLC unit (Pharmacia, Freiburg, Germany). For size-exclusion chromatography, a Pharmacia Superdex 200 column (XK 16/60) was loaded with 5 mg of membrane protein preparation in buffer A (100 mmol of Tris HCl, pH 7.5, 2 mmol of EDTA, 40 mmol of NaCl, 1% Triton X-100). The column eluate was fractionated and studied in a Western-blot analysis in a reaction with antibody SC-1. Positive fractions were loaded on a monoQ-column with use of buffer A. The bonded proteins were fractionated with a linear gradient with use of buffer B (100 mmol of tris-HCl, pH 7.5, 1 M of NaCl, 2 mmol of EDTA, 1% Triton X100) and studied by SDS-polyacrylamide-gel electrophoresis and staining with Coomassie or Western-blot analysis. Positive strips were cut out from the gel and sequenced.

1.4 Preparation of Cell Lysates after Induction with SC-1

Cell line 23132 was cultivated in 100 mm cell culture dishes until a subconfluence occurred. Antibody SC-1 was added in a final concentration of 30 μg/ml for the time period indicated in each case. Then, the culture plates were washed once with PBS, and the cells were lysed directly with SDS buffer (50 mmol of tris-HCl, pH 6.8, 10 mmol of dithiothreitol, 2% (w/v) SDS, 10% (v/v) glycerol). The cell residues were collected with a rubber scraper.

1.5 Gel Electrophoresis and Blots

The SDS-polyacrylamide-gel electrophoresis under reducing conditions and the Western-blotting of proteins were performed with use of standard protocols as described in Vollmers et al. (Cancer 79 (1997), 433-440). Nitrocellulose membranes were blocked with PBS with the addition of 0.1% Tween-20 and 2% skim milk powder or 3% bovine serum albumin (for determination of phosphorylation) and then incubated for one hour with the primary antibody. The antibodies were used in the following dilutions: SC-1 (human) 10 μg/ml or 15 μg/ml; anti-caspase-3 or -8 (goat) (Santa Cruz, Heidelberg, Germany) 5 μg/ml, streptavidin anti-phosphotyrosine conjugate (clone PT-66) 1:20,000 and streptavidin anti-phosphoserine conjugate (clone PSR-45) 1:30,000 (Sigma, Munich, Germany), mouse-anti-topoisomerase IIα-antibody 1:1,000 (Neomarkers, Baesweiler, Germany), anti-c-myc-antibody 1:1,000 (Santa Cruz, Heidelberg, Germany) and anti-PARP-antibody 1:1,000 (Pharmingen, Heidelberg, Germany). The secondary antibody peroxidase-rabbit-anti-human-IgM conjugate or rabbit-anti-goat-antibody (Dianova, Hamburg, Germany) and peroxidase-conjugated extravidin (Sigma) were detected with the SuperSignal Chemiluminescence Kit of Pierce (KMF, St. Augustin, Germany).

1.6 Protein Sequencing

A protein strip with an apparent molecular weight of 82 kD was isolated by one-dimensional polyacrylamide gel electrophoreses and made visible by staining with Coomassie. The p82-strip was cleaved in the gel with trypsin (Boehringer Mannheim, non-modified, sequencing quality) as described in Shevchenko et al., (Anal. Chem. 68 (1996), 850-858). The non-separated pool of tryptic peptides was sequenced by nanoelectrospray-tandem-mass spectrometry as described by Wilm et al. (Nature 379 (1996), 466-469). The sequencing was carried out on an API III Triple Quadrupol Mass Spectrometer (PE Sciex, Ontario, Canada). The sequences of the peptide fragments were assembled with use of the tandem-mass spectrometric data and categorized in the respective proteins by data bank research.

1.7 RT-PCR

The cDNA synthesis of the entire RNA of tumor cells 23132 was carried out with 5 μg of total RNA with use of M-MLV reverse transcriptase (Gibco BRL, Eggenstein, Germany) according to the information of the manufacturer. The PCR reactions were performed in a reaction volume of 25 μl with 1.75 mmol of $MgCl_2$, 0.4 pM of primer, 200 μM of each dNTP and 1 U of Taq polymerase (MBI Fermentas, St. Leon-Rot, Germany).

The following PCR products were produced:

CD55 (640 by fragment from the sequence range of by 382 to 1022), p53 fragment 1 (850 by fragment from the sequence range of 91 to 940), p53-fragment 2 (800 by from the sequence range of 492 to 1294).

1.8 Cloning Procedures

The PCR products were purified from an agarose gel with use of the Jetsorb gel-extraction kit (Genomed, Bad Oeynhausen, Germany). The cloning of the PCR fragments was carried out with the pCR script Amp SK (+) cloning kit (Stratagene, Heidelberg, Germany).

The cloning of the antisense vector pHOOK2-CD55-anti was carried out by smoothing of the CD55-PCR product with Pfu-polymerase and cloning in the expression vector pHOOK2 that is cut with SmaI (Invitrogen, Leek, The Netherlands). A clone with antisense direction of the insertion under control of the $P_{CMV}$ promoter was selected for the antisense experiment.

1.9 DNA Sequencing

Eight positive clones were sequenced with use of the DyeDeoxy Termination Cycle Sequencing Kit (Applied BioSystems, Inc., Weiterstadt, Germany), and the automated DNA sequencer ABIPrism 373 was analyzed. Both strands were sequenced with use of T3 and T7 primers. The sequences were analyzed with use of the computer program DNASIS and BLAST.

1.10 Transfection

For transfection experiments, $2.5 \times 10^7$ dissolved cells in tris-buffered salt solution (TBS) were washed and resuspended in 400 μl of TBS. After 10 μg of plasmid DNA was added, the cells were pulsed with 240 V, 960 nF with an electroporation device of BioRad (Munich, Germany). $5 \times 10^5$ transfixed cells were saturated on a 60 mm cell culture dish and incubated for 24 hours as described above. The apoptosis was induced by adding 50 μg/ml of purified SC-1 antibody to the growth medium. After 24 hours, the cells were treated with trypsin and used for the production of cytospins.

1.11 Phospholipase Test

Dissolved and deleted cells were resuspended in RPMI-1640 with additives and incubated for 90 minutes at 37° C. After this rest period, 20 mU/ml of PI-PLC (Boehringer Mannheim) was added, and the cells were incubated for another 60 minutes. Finally, the cells were washed and used for the production of cytospins.

1.12 Glycosidase Test

Dissolved and washed cells were resuspended in RPMI-1640 with 10% fetal calf serum, incubated for 1 hour in ice, then counted, and cytospins were produced. After air drying, the cytospin preparations were fixed with acetone (10 minutes), washed and incubated with 20 μU/ml of O-glycosidase or 5 mU/ml of N-glycosidase (Boehringer Mannheim) for 4 hours at 37° C.

1.13 Immunohistochemical Staining

The following antibodies were used for the immunohistochemical staining: purified antibody SC-1, anti-CEA-antibody (DAKO, Hamburg, Germany), Anti-EMA-antibody (Loxo, Dossenheim, Germany) and anti-CD55-antibody (Biozol, Eiching, Germany). The acetone setting and staining of the cytospin preparations were carried out as described by Vollmers et al. (Hum. Antibodies Hybridomas 7 (1996), 37-41).

For immunohistochemical staining of apoptotic cells, cells that were cultivated until subconfluence occurred were incubated with purified antibody SC-1 (diluted to 50 μg/ml) in full growth medium for up to 96 hours. Adherent and dissolved cells were collected, centrifuged and resuspended in complete growth medium. After cells were counted, cytospin preparations were produced and dried overnight at room temperature. In studying the cleavage of cytokeratin 18 in vivo, biopsies were taken from patients before treatment with SC-1 and tissue sections after treatment and gastrectomy as described in Vollmers et al., (Oncol. Rep. 5 (1998), 549-552).

The cytospins were blocked with bovine serum albumin (15 mg/ml) in phosphate-buffered salt solution (PBS) for 30 minutes. Then, incubation was carried out for 1 hour with SC-1 supernatant, M30 cyto death-antibody (Roche Biochemicals, Mannheim, Germany) or mouse-anti-cytokeratin 18 antibody (DAKO, Hamburg, Germany) diluted at 1:15. Then, it was washed for 30 minutes in PBS, followed by incubation with peroxidase-labeled rabbit-anti-mouse or rabbit-anti-human conjugate (DAKO), diluted at 1:25. After 30 minutes of washing with PBS, staining was carried out with diaminobenzidine (0.05%) and hydrogen peroxide (0.02%) for 3 minutes at room temperature. The reaction was stopped with tap water, and the tissue sections were counterstained with hematoxylin.

1.14 Apoptosis Tests

Cytospin preparations (5,000 cells/slides) were fixed in acetone and then washed with TBS. Then, they were stained with the FragE1-Klenow DNA-Fragmentation Kit (Calbiochem-Novabiochem, Bad Soden, Germany) according to manufacturer information.

An ELISA for detection of apoptosis was performed with use of the Cell Death Detection® Kit (Roche Biochemicals) according to the manufacturer's instructions.

1.15 MTT Test

The MTT proliferation test (Carmichael et al., Cancer Res. 47 (1987), 936-942) for determining the apoptosis activity of antibody SC-1 on gastric carcinoma cells was performed as described in Vollmers et al. (Cancer 76 (1995), 550-558). The determination of cell growth was carried out by the mitochondrial hydroxylase test (Mossmann, J. Immunol. Meth. 65 (1983), 55-63). The percentage portion of apoptotic cells was determined from the absorption of the cells that were induced with SC-1 and the control that was not induced with SC-1 (Vercammen et al., J. Exp. Med. 188 (1998), 919-930).

1.16 Caspase-3 and Caspase-8 Tests

The activation of caspase-8 and caspase-3 was determined with the ApoAlere™ Caspase Fluorescence Test Kit (Clontech, Heidelberg, Germany). In this connection, $1 \times 10^6$ cells with 40 μg/ml of SC-1 were incubated for 7 or 20 hours. Then, the cells were collected, resuspended in cell-lysis buffer, and the caspase activity was determined according to manufacturer information.

1.17 Determination of Intracellular Free Calcium [$Ca^{2+}$]

The determination of the intracellular free calcium concentration was determined with use of the calcium-sensitive dye Fura-2-AM as described by Grykiewicz et al. (J. Biol. Chem. 260 (1985), 3440-3450). In this connection, the cells were incubated for 15 minutes with a Fura-2-AM in Ringer's solution that contains a final concentration of $5 \times 10^{-6}$ M (122.5 mmol of NaCl, 5.4 mmol of KCl, 1.2 mmol of $CaCl_2$, 0.8 mmol of $MgCl_2$, 1 mmol of $NaH_2PO_4$, 5.5 mmol of glucose, 10 mmol of HEPES, pH 7.4). After flushing, the slides were examined with an Axiovert 100 TV microscope (400-fold magnification). The fluorescence signal was measured at 500 nm with excitation wavelengths that alternate between 334 and 380 nm with use of a 100-W xenon lamp and an automatic filter changing device (Zeiss, Germany). The concentration of intracellular free calcium was calculated according to the method of Grynkiewicz et al. (supra) with the assumption of a dissociation constant of 225 nmol/l. The maximum and minimum fluorescence ratios ($R_{max}$ and $R_{min}$) were measured after calibrating solutions were added. $R_{max}$ was determined after a Ringer's solution with 3 mmol $Ca^{2+}$ and $10^{-6}$ M of ionomycin was added. $R_{min}$ was determined in the presence of a $Ca^{2+}$-free Ringer's solution with 3 mmol of EGTA and $10^{-6}$ M of ionomycin.

1.18 Inhibition of Intracellular Calcium Release

Cells were washed once with phosphate-buffered salt solution and washed for 24 hours in calcium-free DMEM medium without fetal calf serum (FCS). Then, purified SC-1 antibody was added until a final concentration of 40 µg/ml was reached. As a control, the same cells were used without SC-1. The cells were incubated in a wet incubator for another 24 or 48 hours and then fixed with 3% glutaric aldehyde. The cell culture plates were then examined for morphological changes with the aid of a light microscope.

2. Results 2.1 Purification of the SC-1-Receptor CD55

Figure 1:
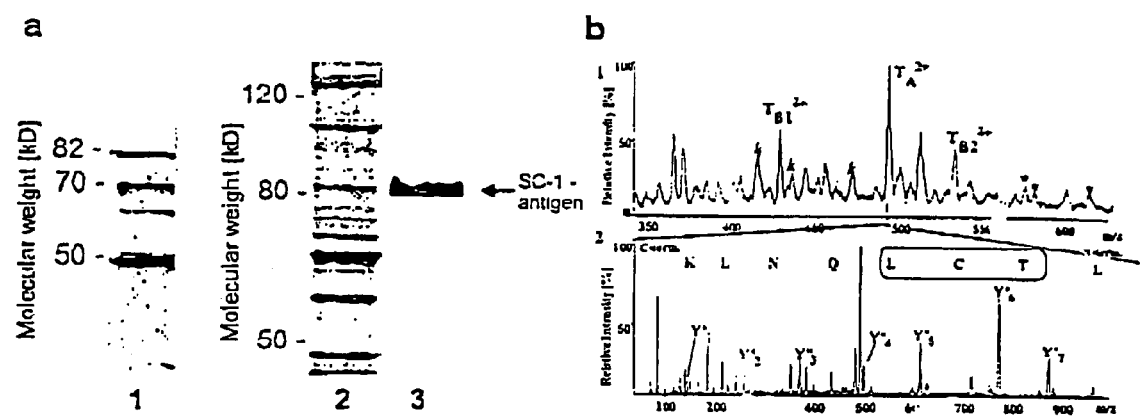

In Western-blot analysis of extracts from total cell lysates of gastric carcinoma cell line 23132, which had been produced under low-salt conditions (100 mmol of NaCl), antibody SC-1 reacted with a protein with a relative molecular mass of about 50 kD. By altering the stringency (1 M of NaCl) and with use of membrane preparations, it was possible to detect other proteins with approximately 70 kD and approximately 82 kD (FIG. 1a, trace 1). These proteins were isolated from the membrane fractions and purified by sequential size-exclusion and anion-exchange chromatography (FIG. 1a, traces 2, 3). The molecules were cut out from SDS-polyacrylamide gels and sequenced.

The 50 kD protein was identified as a dihydrolipoamide-succinyltransferase (gene bank access no. L37418), and the 70 kD protein was identified as the human Lupus p70 auto-antigen protein (gene bank access no. J04611). These proteins are cytoplasmatic or nuclear antigens. Since antibody SC-1 in immunohistochemical studies binds only to cell surface antigens, the reactivity can presumably be attributed to unspecific binding based on the protein denaturation during the Western-blot analysis.

The 82 kD protein was identified as CD55 (DAF, gene bank access no. M31516, FIG. 1b, sections 1 and 2). In humans, CD55 exists in two genetically specified isoforms (secreted DAF-A and membrane-bonded DAF-B), which are produced by differential splicing (Caras et al., Nature 325 (1987), 545-549). It was found by RT-PCR analysis that cell line 23132 expresses only the membrane-anchored DAF-B isoform.

2.2 Phospholipase Treatment

Figure 2:
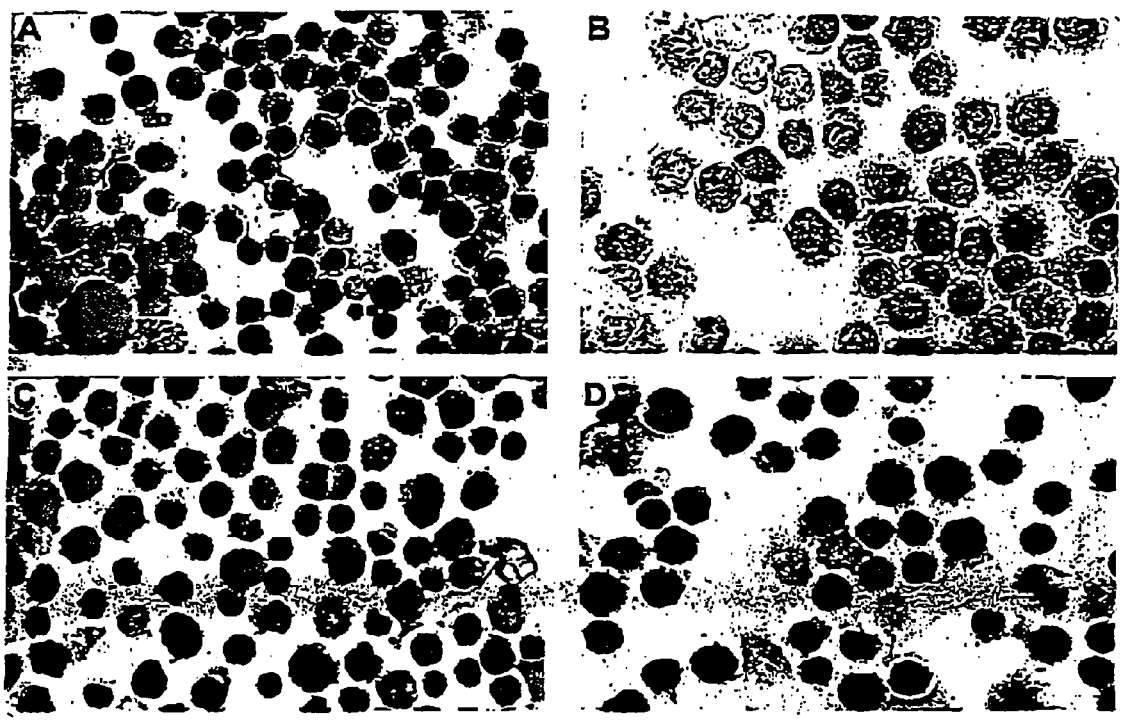
Figure 3:
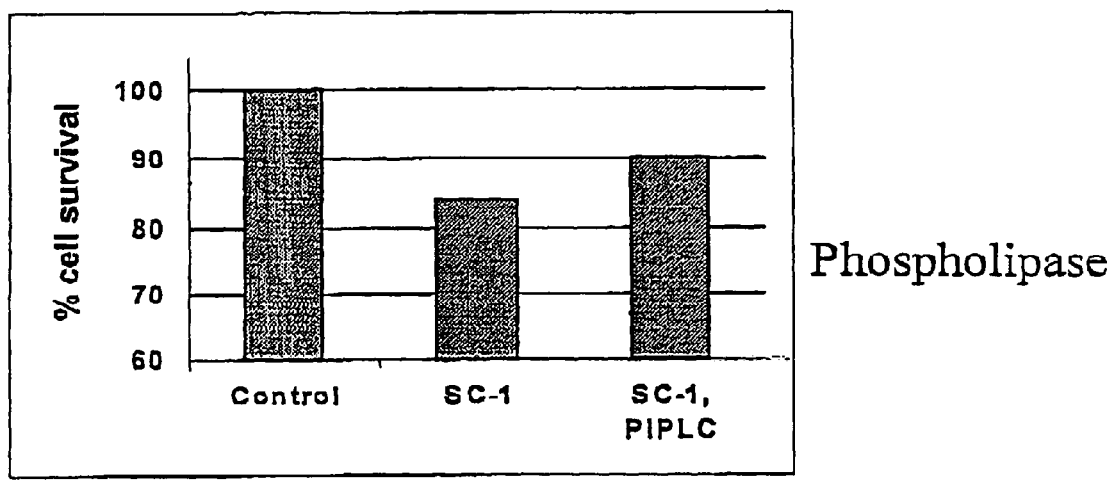

The influence of a cleavage of the glycosidphosphatidylinositol (GPI)-anchor on the bond of SC-1 was analyzed by immunohistochemical studies and in the MTT-proliferation test. In this connection, the GPI-anchor was cleaved by incubation with phosphatidylinositol-specific phospholipase C (PI-PLC). Cytospins of cells that were treated with PI-PLC and untreated cells were stained immunohistochemically with SC-1, anti-CD55 and anti-EMA (epithelial-membrane-antigen). A comparison with untreated cells (FIG. 2a) shows a loss in staining intensity in cells that are treated with PI-PLC and stained with SC-1 (FIG. 2b). In the case of staining with anti-EMA (FIG. 2c, d), no difference in staining was found, which indicates that the PI-PLC treatment has no effect on non-GPI-anchored membrane proteins. In the MTT test, a treatment of cells with phospholipase C resulted in a significant reduction ($p \leq 0.05$) of the apoptotic cells (FIG. 3).

2.3 Transfection with Antisense-CD55 RNA

Figure 4:
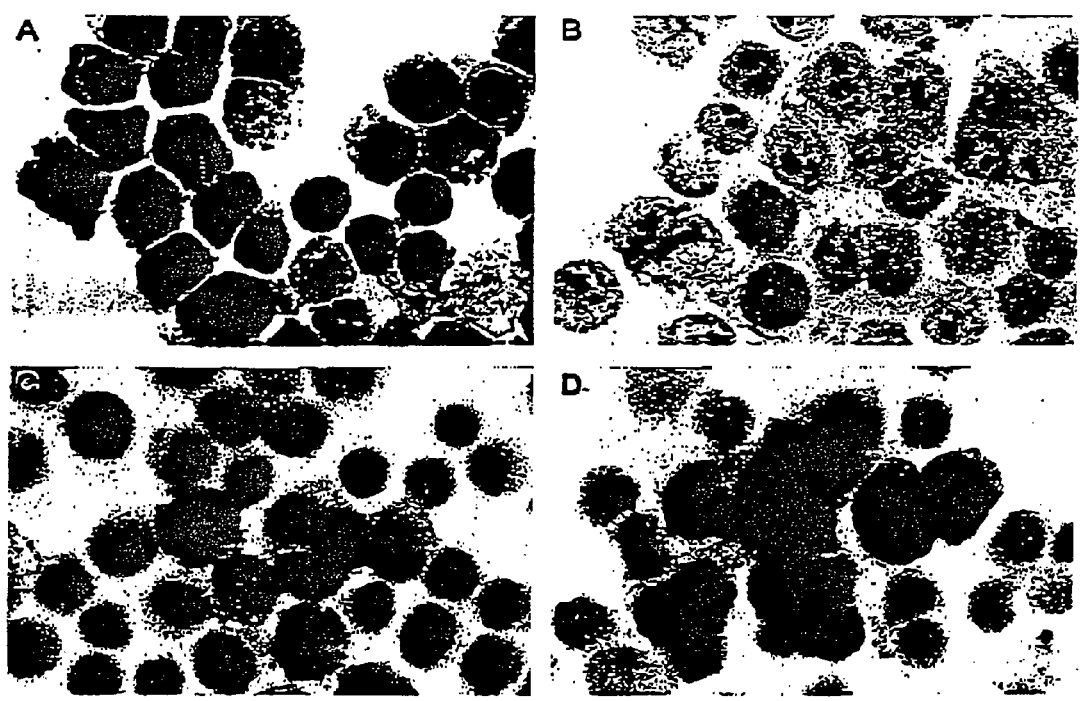

Cell line 23132 was transiently transfixed with the CD55 antisense-vector pHOOK2-CD55anti and the control vector pHOOK2 by electroporation. First, cytospins of transfixed cells were immunohistochemically stained with SC-1, anti-CD55 and anti-CEA (carcino-embryonal antigen). The cells that were transfixed with the control vector showed an intensive staining with SC-1 and CEA (FIG. 4a, c). In cells that were stained with the CD55 antisense vector, almost no staining with SC-1 was found (FIG. 4b). The staining with anti-CEA-antibodies showed that the expression pattern of the CEA (also GPI-anchored) is not affected by the transfection with the antisense vector. Consequently, the expression of CD55 was reduced specifically based on the expression of the antisense RNA.

Figure 5:
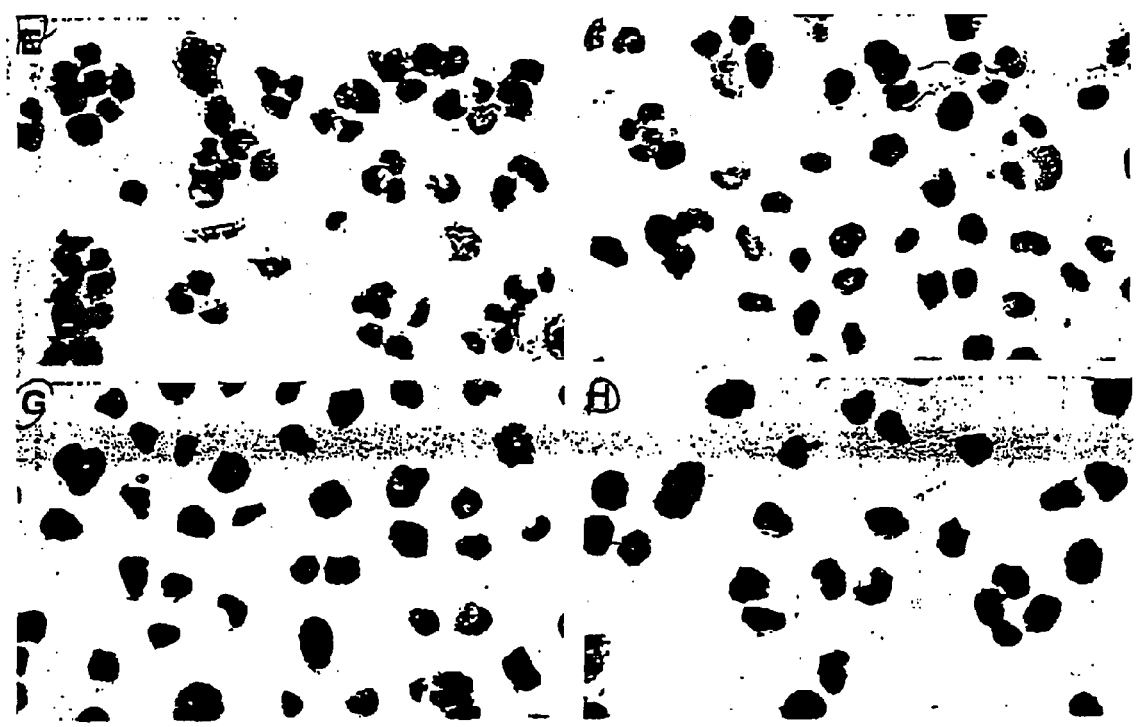

To analyze whether the expression of antisense-CD55 RNA also inhibits the SC-1 induced apoptosis, the cells were incubated for one day after the transfection with and without 30 µg/ml of SC-1 for a period of 24 hours. Cytospins of cells that were transfixed with the antisense vector and the control vector were stained with the FragE1 Klenow DNA Fragmentation Kit for the detection of a DNA-fragmentation induced by apoptosis. While untransfixed cells that are treated with two plasmids show almost no spontaneous apoptosis (FIG. 5e), a considerable reduction in the apoptosis of cells that are transfixed with the CD55 antisense vector (FIG. 5g) in comparison to cells that are transfixed with the control vector (FIG. 5h) is found after incubation with SC-1.

Figure 6:
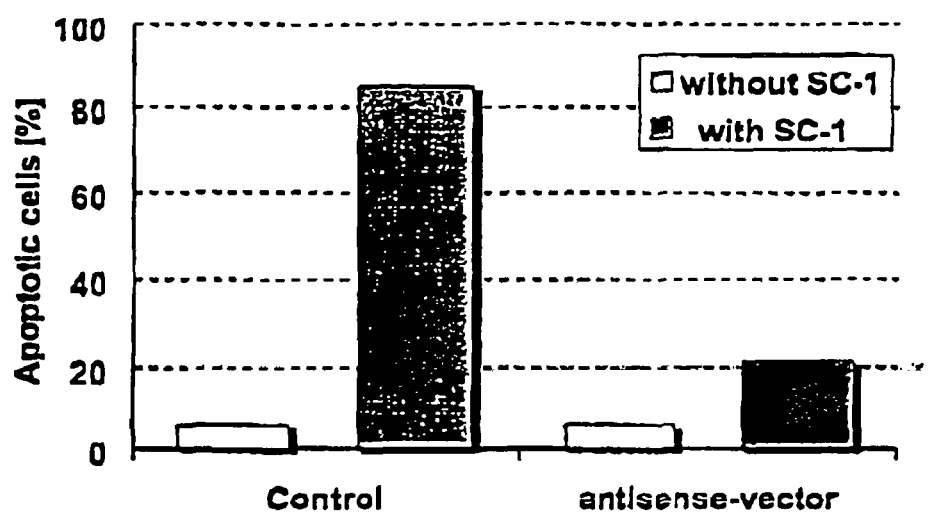

A quantitative determination showed that spontaneous apoptosis in transfixed 23132 cells occurred with a frequency of 6%, while 85% of the cells that were transfixed with the control vector showed an apoptosis after incubation with SC-1. This apoptotic reaction was reduced to 21% by transfection with the CD55 antisense vector (FIG. 6).

2.4 Glycosidase Treatment

Figure 7:
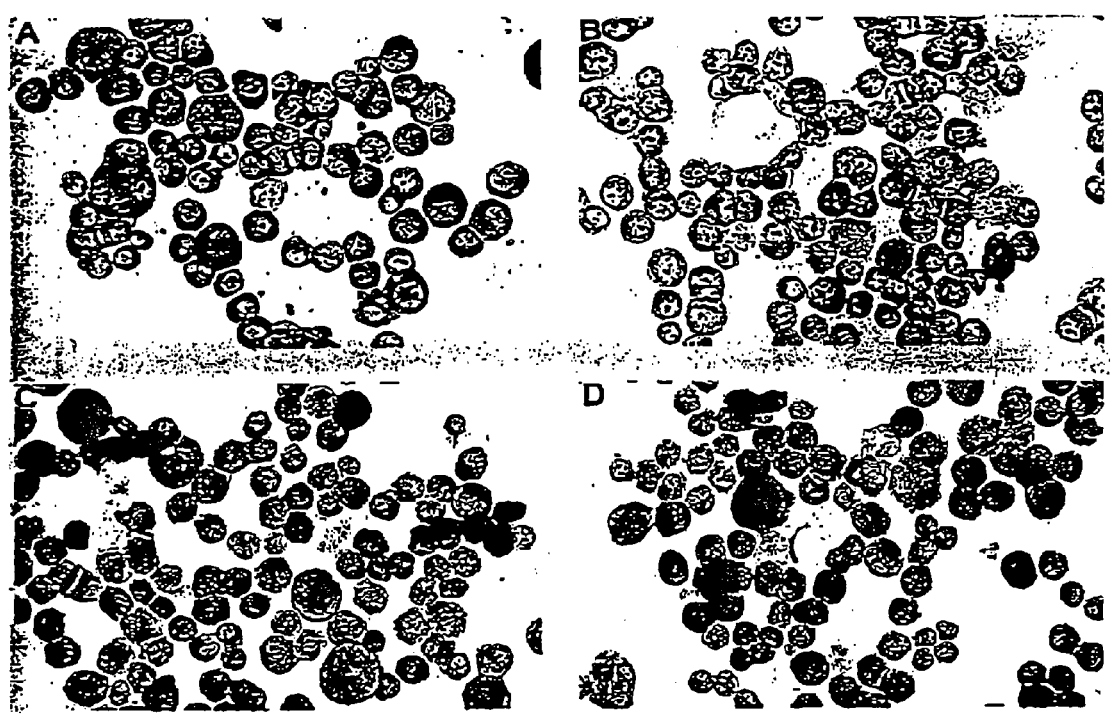

The influence of a protein deglycosylation on the bond of SC-1 to cell line 23132 was studied by incubation of cytospin preparations with O- and N-glycosidases before the immunohistochemical staining. A treatment of cells with N-glycosidase resulted in a significant reduction of the SC-1 staining (FIG. 7b), while a staining with anti-CD55, which detects the proportion of protein in the SCR3 region, was not influenced by protein deglycosylation (FIG. 7d). Incubation with phosphate buffer and a treatment with O-glycosidase had no effect on the SC-1 bond. This shows that the specificity of SC-1 must be located in N-linked sugar radicals and not in the primary protein sequence.

2.5 Cross-linking of CD55/SC-1

Figure 8:
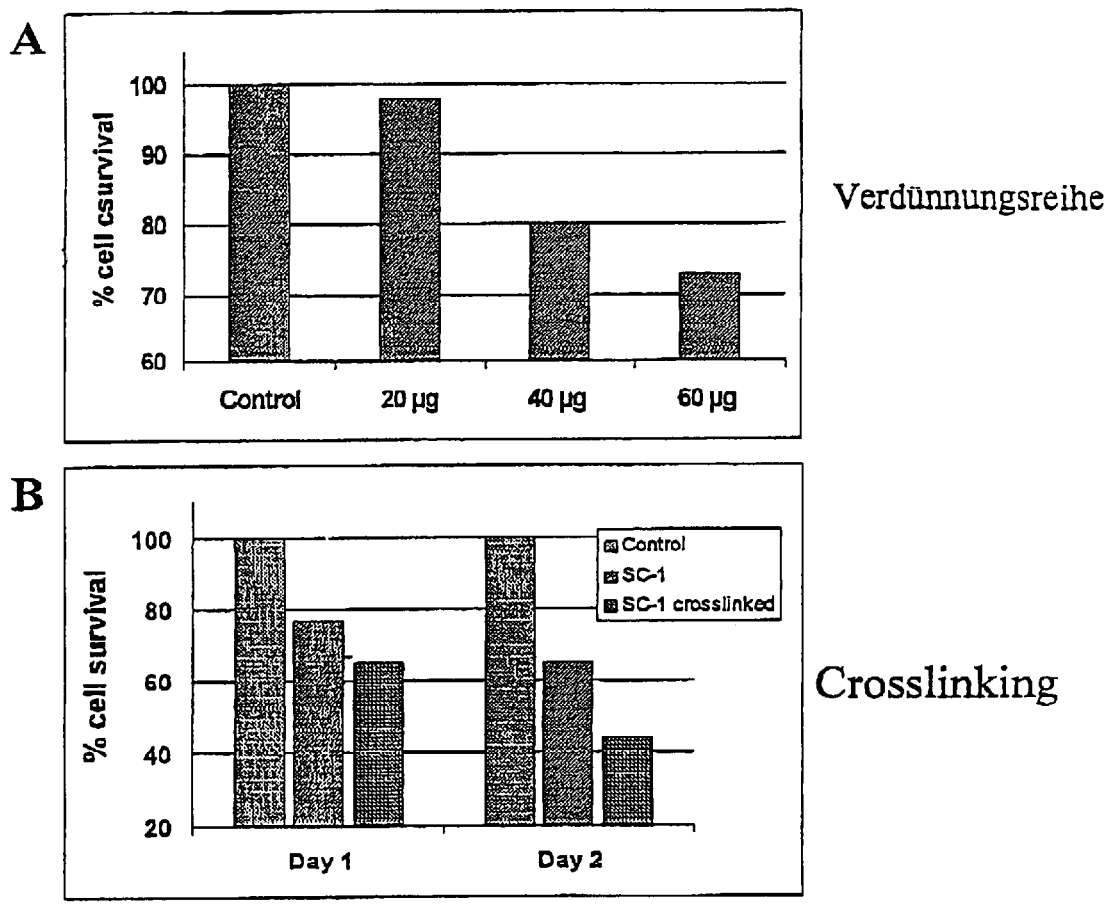

The cells were incubated for 24 hours with increasing quantities of SC-1 to determine the optimum apoptopic activity of SC-1 (FIG. 8a). Then, crosslinking was carried out at a concentration of 40 µg/ml of SC-1 with rabbit-anti-human IgM. After incubation for 48 hours, a 47% higher portion of dead cells than in the control cells that are incubated with SC-1 was found (FIG. 8b).

2.6 Calcium Level

Figure 9:
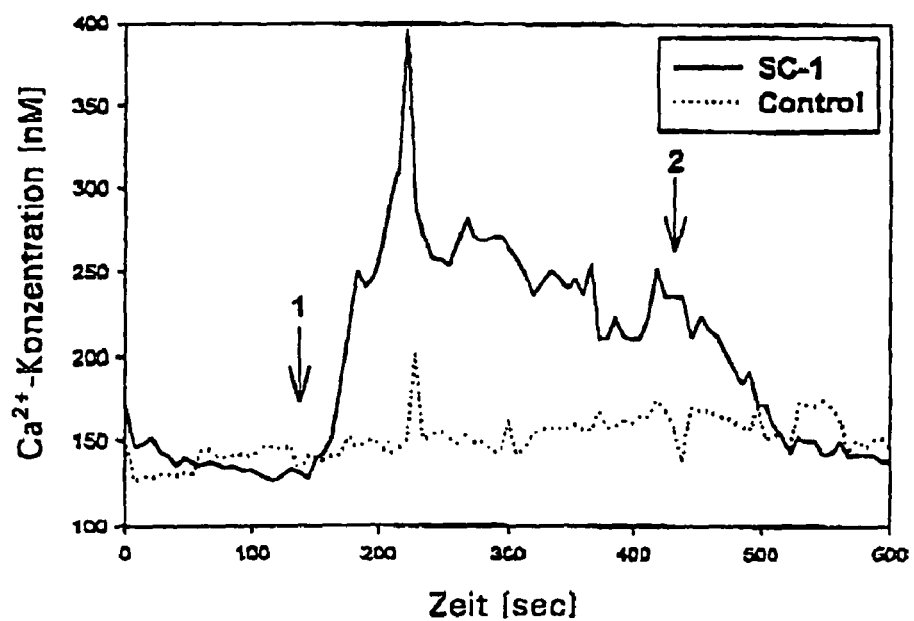

To examine whether the apoptosis that is induced by SC-1 is accompanied by changes of the calcium level, the intracellular calcium concentration of cell line 23132 was determined after induction with SC-1 and control antibodies (unspecific human IgM). In this case, a significant increase of the intracellular calcium concentration was found approximately 1 minute after SC-1 antibody was added, while the control antibody had no effect (FIG. 9).

2.7 Caspase Activity

Figure 10:
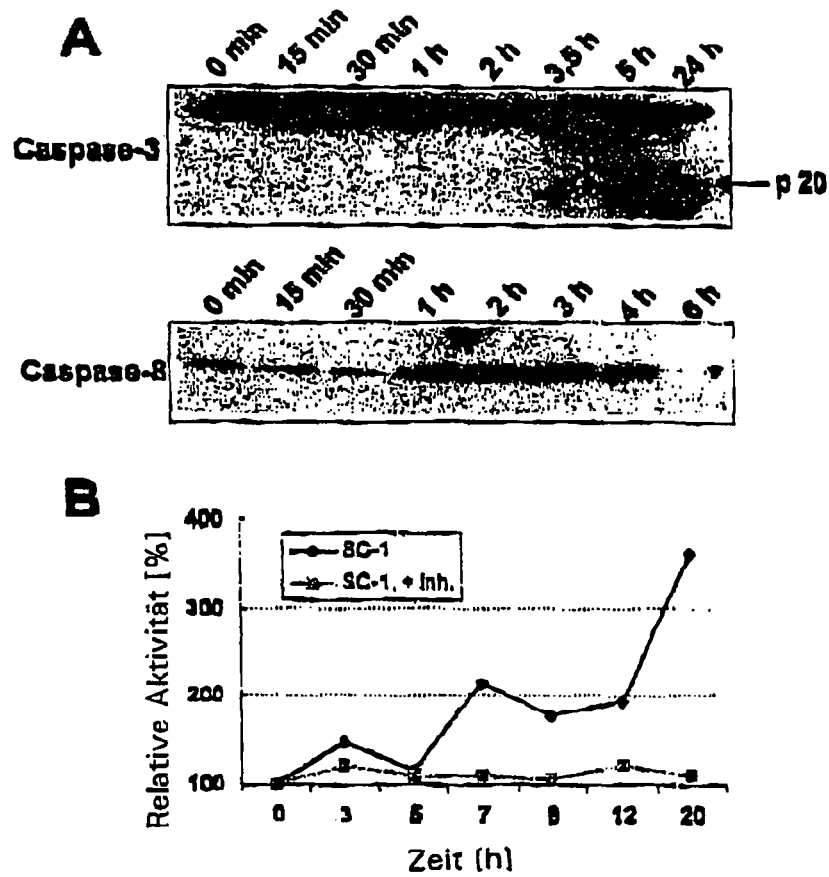

It was found by Western-blot analysis that caspase-3 and caspase-8 are regulated upward after induction of cell line 23132 with SC-1 (FIG. 10a). A proteolytic cleavage that causes the activation of caspases was detected for caspase-3 by identifying cleavage product p20 (FIG. 10a). In caspase-8, a four-fold increase of the activity was found 20 hours after induction with SC-1, which indicates a significant participation of this caspase in the apoptosis process (FIG. 10b).

The addition of the specific caspase-3 inhibitor AC-DEVD-CHO (Alexis Biochemicals, Grünberg, Germany) showed, surprisingly enough with increasing concentration, an increase of apoptosis in the case of determination with the Cell Death Detection® Kit (FIG. 15).

2.8 Protein Phosphorylation

Figure 11:
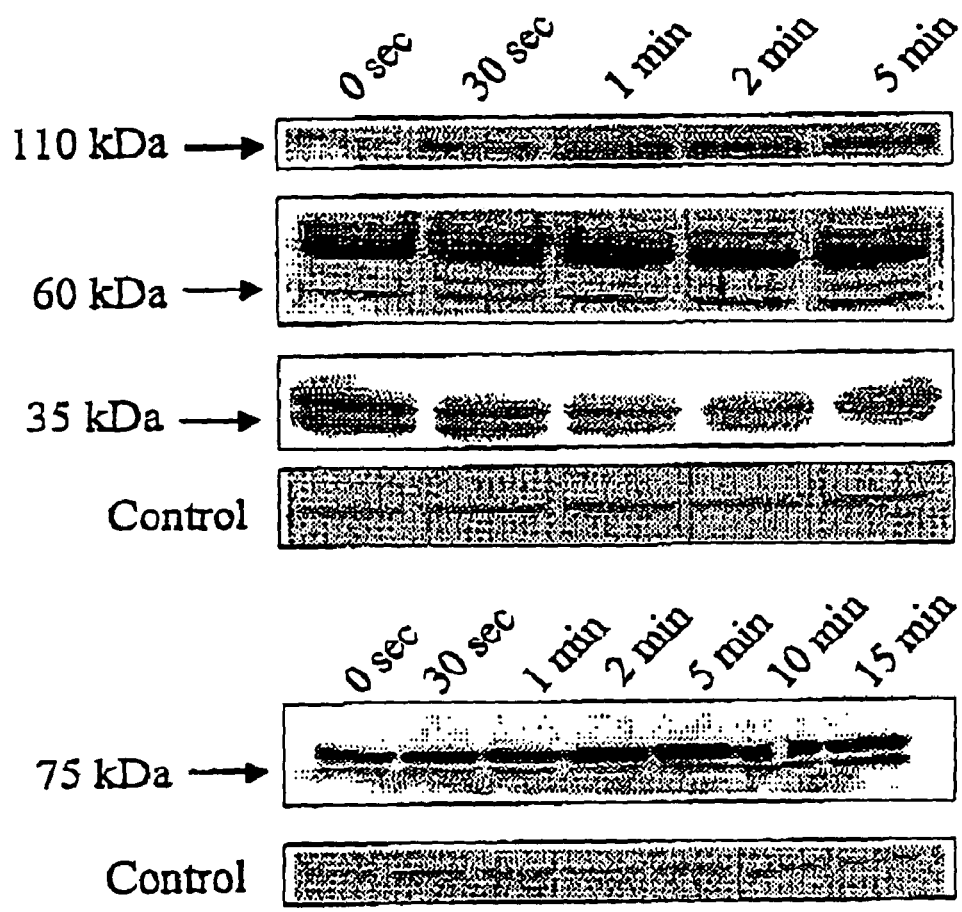

After induction of cells with 40 µg/ml of SC-1 antibodies, the phosphorylation pattern was examined by Western-blot analysis of cytoplasmatic and membrane extracts. In this case, an early tyrosine phosphorylation of 110 kD and 60 kD of proteins was found 30 to 60 seconds after apoptosis was induced (FIG. 11). The 60 kD protein was found only in the cytoplasma, while the 110 kD protein could be detected both in the plasma and in the membrane extract. In addition, a slow tyrosine phosphorylation of a cytoplasmatic 75 kD protein with a maximum was found after 10 minutes, and the complete disappearance of the serine phosphorylation of a 35 kD protein was found 10 minutes after induction.

2.9 Expression and Sequencing of p53

Figure 12:
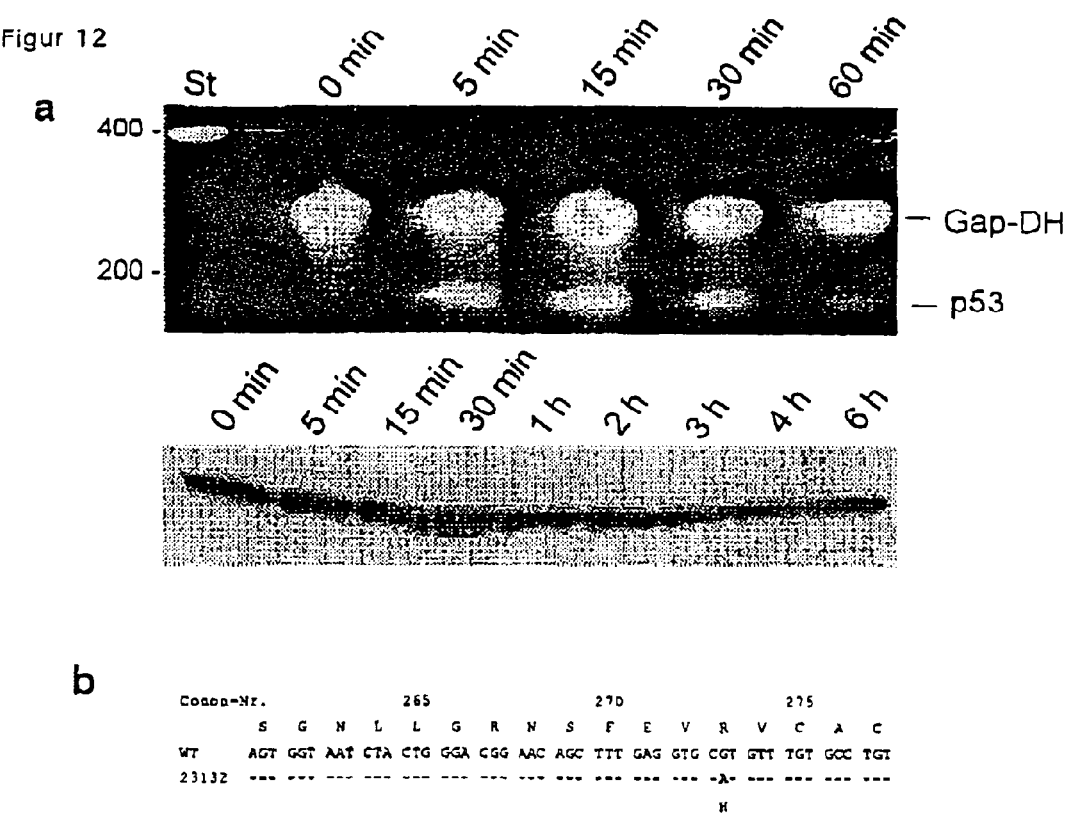
Figure 12:
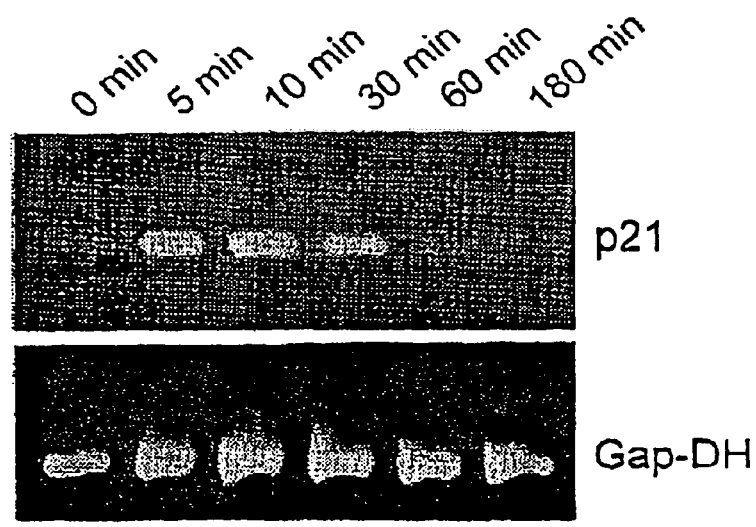

To study the role of p53 in the case of SC-1-induced apoptosis, the frequency of the mRNA by RT-PCR and the gene product was determined by Western-blot analysis after induction. In this case, a considerable increase of the mRNA concentration was found. On the protein plane, however, a constant and not significantly altered high concentration of the p53 gene product was found (FIG. 12a).

The DNA-sequence of p53 in cell line 23132 was determined by amplification of two p53 fragments of cDNA with specific primers, cloning of the PCR-fragments and sequencing of eight clones. All clones with insertions spanning Exon 8 showed a mutation in codon 273, which resulted in an amino acid exchange of arginine to histidine (FIG. 12b). This is a dominant negative mutation, which frequently occurs in gastric adenocarcinomas.

2.10 Expression of p21

Figure 13:
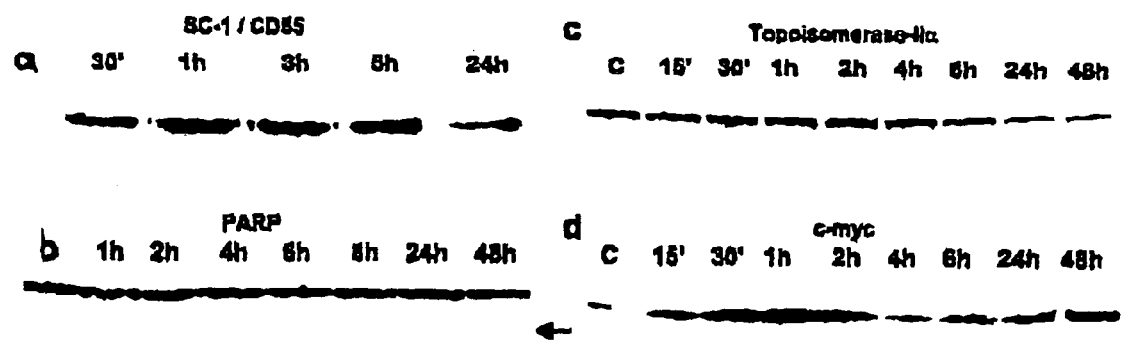
FIG. 13 shows: an expression analysis of p21. After apoptosis is induced, an increase of the p21 mRNA concentration was found.

Protein p21 is a molecule that is associated with the expression of p53. A test of the expression of p21 in gastric carcinoma cell line 23132 after treatment with SC-1 yielded an increase after 5 minutes followed by a reduction after 60 minutes (FIG. 13).

2.11 Expression of CD55/DAF after Apoptosis is Induced

Figure 14:
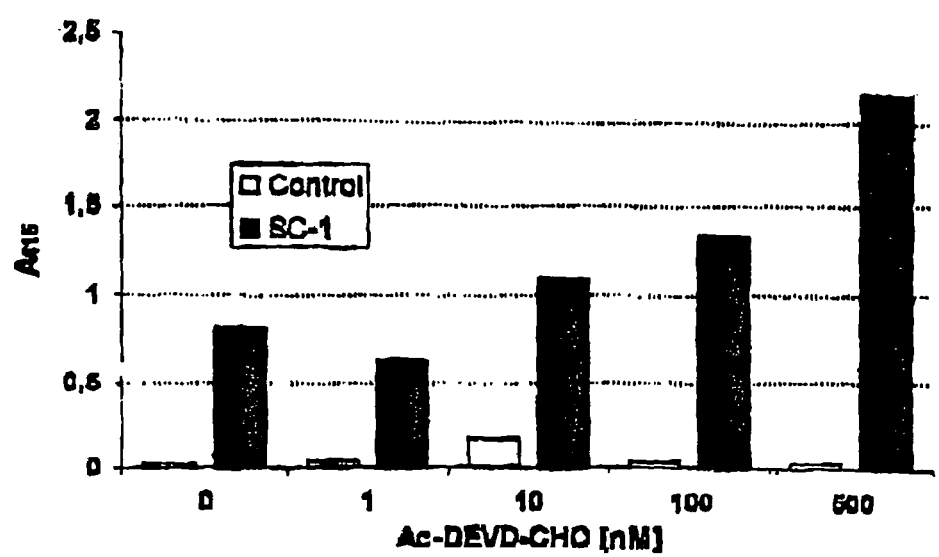
FIG. 14 shows: a Western-blot analysis of SC-1-induced cells.

The expression pattern of CD55/DAF was studied after apoptosis was induced by 50 µg/ml of SC-1 using immunohistochemical staining of cytospin preparations with antibody SC-1. While non-induced cells exhibit a slight membrane staining with antibody SC-1, cells that were induced with SC-1 showed intensive membrane staining 12 hours after apoptosis was induced. This indicates an increase of the CD55/DAF presentation on the cell surface after the antibody is bonded to the cells. This membrane staining disappears after 48 hours, and a diffuse cytoplasmatic staining can be detected. This staining is also found with reduced intensity after 96 hours. The increase in the CD55/DAF expression was also found in a Western Blot analysis with membrane extracts of apoptotic cells after SC-1 induction. While CD55/DAF cannot be detected in non-induced cells, the CD55/DAF expression increases 1 hour to 6 hours after induction. After 24 hours, the expression of CD55/DAF decreases, but it is always still higher than in non-induced cells (FIG. 14a).

2.12 Cleavage of Cytokeratin 18

The degradation of apoptotic cells accompanies the proteolytic cleavage of cytokeratin 18. The cleavage of cytokeratin 18 in cell line 23132 after SC-1-induced apoptosis and in primary tumors of patients who had been treated with 20 mg of SC-1 for 48 hours before a tumor resection was studied. An M30 cyto death staining showed a small quantity of apoptotic cells without inducing apoptosis, while the number of apoptotic cells increased up to 96 hours.

2.13 Molecular Analysis of SC-1-Apoptosis

Consistent with the immunohistochemical staining, the biochemical analysis showed an increase of the CD55/DAF molecule, followed by a slight reduction after 24 hours of incubation with SC-1 (FIG. 14a). The cleavage of PARP was studied by Western Blot analysis with use of total cell extracts from SC-1-induced cells and murine anti-PARP antibodies. In five independent experiments, no cleavage of PARP was found that would be detected by the occurrence of an 85 kD cleavage product (Lazebnik et al., Nature 371 (1994), 346-347) (FIG. 14b).

To study changes in the cell cycle after apoptosis is induced, the expression of topoisomerase IIα by Western Blot analysis was determined. Topoisomerase IIα is a key enzyme in the cell cycle, which is involved in DNA replication (Watt and Hickson, Biochem. J. 303 (1994), 681-695). The reduced expression of topoisomerase IIα according to SC-1-induced apoptosis therefore shows a cell cycle arrest for at least one portion of cells (FIG. 14c).

Transcription factor c-myc is involved in various apoptotic processes and can induce an apoptosis by transfection in cells (Evan et al., Cell 69 (1992), 119-128). A study of the expression pattern of c-myc after SC-1-induced apoptosis showed an increased expression 15 minutes after apoptosis was induced followed by a reduction after 4 hours (FIG. 14d).

2.14 Action of a Reduction of the Extracellular and Intracellular Calcium Concentration in Apoptosis It was examined whether $Ca^{2+}$ ions from the cell culture medium are taken up or are released from intracellular $Ca^{2+}$ reservoirs. To determine whether $Ca^{2+}$ is taken up from the culture medium, the cells were incubated for 24 hours in serum-free and $Ca^{2+}$-free DMEM medium. Then, purified SC-1-antibody was added at a final concentration of 40 µg/ml and incubated for another 24 hours. The cells were then fixed in 3% glutaric aldehyde and studied in a rotated light microscope. Compared to control cells (not induced with SC-1), SC-1-induced cells showed morphological changes characteristic of an apoptosis and comparable with cells that would have been incubated with SC-1 in RPMI medium with the addition of 10% FCS.

The effect of $Ca^{2+}$ from intracellular $Ca^{2+}$ reservoirs was studied by incubation of cells (cultivated in serum-free DMEM medium) for 5 hours with 50 µM of the cell-permeable chelating agent BAPTA (Alexis Biochemicals, Grünberg, Germany). The cells were incubated for 24 hours with 40 μg/ml of purified SC-1. No detectable changes could be observed in the cell morphology, which indicates that no apoptosis was induced. An inhibition of the apoptosis produced by BAPTA could also be found by ELISA.

2.15 Detection of Apoptosis in Primary Tumors

The administration of antibody. SC-1 to patients with stomach cancer resulted in a clearly detectable tumor-cell-specific apoptosis, as was detected by in-situ nucleus staining (FIG. 16). While no apoptosis (FIG. 17a) or the presence of an intact tumor without regression (FIG. 17c) was found in tumor biopsies that were taken before SC-1 was administered, the primary tumor showed strong apoptosis (FIG. 17b) or a strong regression (FIG. 17d) after SC-1 was administered.

The invention claimed is:

1. A purified glycoprotein comprising the human amino acid primary structure of CD55 and a tumor-specific N-linked glycostructure, wherein said glycoprotein has an apparent molecular weight of about 82 kD in sodium dodecyl sulfate polyacrylamide gel electrophoresis and is a glycoprotein present on adenocarcinoma cell line 23132 (DSMZ Accession No. DSM ACC 201), but not on a normal cell.

2. A process for obtaining a glycoprotein comprising the human amino acid primary structure of CD55 and a tumor-specific N-linked glycostructure, the process comprising producing a membrane preparation from cells of the human adenocarcinoma cell line 23132, and obtaining the glycoprotein therefrom by size-exclusion chromatography, wherein the glycoprotein has an apparent molecular weight of about 82 kD in sodium dodecyl sulfate polyacrylamide gel electrophoresis, and is a glycoprotein present on adenocarcinoma cell line 23132 (DSMZ Accession No. DSM ACC 201), but not on a normal cell.

3. A process for obtaining a glycoprotein comprising the human amino acid primary structure of CD55 and a tumor-specific N-linked glycostructure, the process comprising producing a membrane preparation from cells of the human adenocarcinoma cell line 23132, and obtaining the glycoprotein therefrom by anion-exchange chromatography, wherein the glycoprotein has an apparent molecular weight of about 82 kD in sodium dodecyl sulfate polyacrylamide gel electrophoresis, and is a glycoprotein present on adenocarcinoma cell line 23132 (DSMZ Accession No. DSM ACC 201), but not on a normal cell.

4. The purified glycoprotein of claim 1, wherein said glycoprotein, if present on a cell and bound by an antibody that is specific for said glycostructure, results in apoptosis of said cell.

5. The purified glycoprotein of claim 4, wherein binding of said antibody to said glycostructure results in cleavage of cytokeratin 18 in said cell.

6. The purified glycoprotein of claim 4, wherein binding of said antibody to said glycostructure results in increased c-myc expression in said cell.

7. The purified glycoprotein of claim 4, wherein binding of said antibody to said glycostructure results in decreased topoisomerase IIα expression in said cell.

8. The purified glycoprotein of claim 4, wherein binding of said antibody to said glycostructure results in an increase in intracellular $Ca^{2+}$ concentration in said cell.

9. The purified glycoprotein of claim 4, wherein binding of said antibody to said glycostructure does not induce cleavage of poly(ADP-ribose)-polymerase in said cell.

10. A purified glycoprotein comprising the human amino acid primary structure of CD55 and a tumor-specific glycostructure obtained by the process of claim 2.

11. A purified glycoprotein comprising the human amino acid primary structure of CD55 and a tumor-specific glycostructure obtained by the process of claim 3.

12. A purified glycoprotein comprising a section of a glycosylated human CD55 protein expressed by adenocarcinoma cell line 23132 (DSMZ Accession No. DSM ACC 201), but not by a normal cell, wherein said glycosylated human CD55 protein has an apparent molecular weight of about 82 kD in sodium dodecyl sulfate polyacrylamide gel electrophoresis and wherein said section of said glycosylated human CD55 protein comprises a tumor-specific N-linked glycostructure.

13. The purified glycoprotein of claim 12, wherein an antibody that specifically binds said tumor-specific N-linked glycostructure of said section, upon binding, induces apoptosis of a cell expressing said glycosylated human CD55 protein.

14. The purified glycoprotein of claim 13, wherein binding of said antibody to said glycostructure results in cleavage of cytokeratin 18 in said cell.

15. The purified glycoprotein of claim 13, wherein binding of said antibody to said glycostructure results in increased c-myc expression in said cell.

16. The purified glycoprotein of claim 13, wherein binding of said antibody to said glycostructure results in decreased topoisomerase IIα expression in said cell.

17. The purified glycoprotein of claim 13, wherein binding of said antibody to said glycostructure results in an increase in intracellular $Ca^{2+}$ concentration in said cell.

18. The purified glycoprotein of claim 13, wherein binding of said antibody to said glycostructure does not induce cleavage of poly(ADP-ribose)-polymerase in said cell.

* * * * *

UNITED STATES PATENT AND TRADEMARK OFFICE
CERTIFICATE OF CORRECTION

PATENT NO. : 7,767,787 B1  
APPLICATION NO. : 09/469606  
DATED : August 3, 2010  
INVENTOR(S) : Vollmers et al.

Page 1 of 1

It is certified that error appears in the above-identified patent and that said Letters Patent is hereby corrected as shown below:

Cover Page, under OTHER PUBLICATIONS, in Medof et al., replace "accerlerating" with --accelerating--;

In Knight et al., replace "36-40" with --35-40--;

In Sugita et al., replace "al.,*J*" with --al., *J*--;

Column 2, Line 58, replace "monoclonal Oh antibody" with --monoclonal antibody--;

Line 65, replace "82 kD f protein" with --82 kD of protein--.

Column 3, Line 37, replace "DAF is q, preferably" with --DAF is preferably--;

Column 9, Line 7, replace "640 by fragment" with --640 bp fragment--;

Line 7, replace "range of by 382" with --range of bp 382--;

Line 8, replace "850 by fragment" with --850 bp fragment--;

Line 9, replace "800 by from" with --800 bp from--.

Column 10, Line 53, replace "ApoAlere™" with --ApoAlert™--.

Signed and Sealed this  
Fourth Day of October, 2011

David J. Kappos  
*Director of the United States Patent and Trademark Office*